US010441389B2

(12) United States Patent
Gallacher

(10) Patent No.: US 10,441,389 B2
(45) Date of Patent: Oct. 15, 2019

(54) APPARATUS AND SYSTEM FOR DENTAL MODELING

(71) Applicant: Scott Eric Gallacher, Draper, UT (US)

(72) Inventor: Scott Eric Gallacher, Draper, UT (US)

( * ) Notice: Subject to any disclaimer, the term of this patent is extended or adjusted under 35 U.S.C. 154(b) by 75 days.

(21) Appl. No.: 13/873,206

(22) Filed: Apr. 29, 2013

(65) Prior Publication Data

US 2013/0288193 A1 Oct. 31, 2013

Related U.S. Application Data

(60) Provisional application No. 61/690,561, filed on Jun. 28, 2012, provisional application No. 61/687,554, filed on Apr. 27, 2012.

(51) Int. Cl.
*A61C 11/02* (2006.01)
*A61C 9/00* (2006.01)

(52) U.S. Cl.
CPC .............. *A61C 11/02* (2013.01); *A61C 9/002* (2013.01)

(58) Field of Classification Search
CPC . A61C 11/02; A61C 9/002; A61C 11/00–088; Y10T 403/32

USPC ......................................... 433/57–67; 453/52
See application file for complete search history.

(56) References Cited

U.S. PATENT DOCUMENTS

| 2002/0094505 A1* | 7/2002 | Walter ................... A61C 9/002 433/60 |
| 2003/0147688 A1* | 8/2003 | Hathaway ........... F16C 11/0619 403/90 |
| 2004/0013998 A1* | 1/2004 | Jung ....................... A61C 11/00 433/57 |
| 2004/0131990 A1* | 7/2004 | Doviack ................ A61C 11/02 433/60 |

* cited by examiner

*Primary Examiner* — Yogesh P Patel
(74) *Attorney, Agent, or Firm* — Jason P. Webb; Pearson Butler

(57) ABSTRACT

An apparatus and system is disclosed for dental modeling. The apparatus includes a first tray positioned opposite a second tray and a dearticulating hinge coupling the first tray to the second tray. The dearticulating hinge includes a first hinging element coupled to one of the first tray and the second tray and a second hinging element coupled to the other of the first tray and the second tray. At least one of the first hinging element and the second hinging element includes a disengaging element configured to engage a spur to uncouple the first hinging element from the second hinging element upon extending the first tray and the second tray beyond a predefined angle relative to one another.

12 Claims, 7 Drawing Sheets

APPARATUS AND SYSTEM FOR DENTAL MODELING

CROSS-REFERENCES TO RELATED APPLICATIONS

This application claims the benefit of U.S. Provisional Patent Application No. 61/687,554 entitled "Plastic base pinned dental articulator system" and filed on Apr. 27, 2012 for Scott Eric Gallacher, which is incorporated herein by reference. This application also claims the benefit of U.S. Provisional Patent Application No. 61/690,561 entitled "Dental plastic base pinned articulator system with soft end pin holes" and filed on Jun. 28, 2012 for Scott Eric Gallacher, which is incorporated herein by reference.

FIELD

This subject matter relates to dental modeling and more particularly relates to articulator systems for dental modeling.

BACKGROUND

In the dental field it is imperative that the model made from a patient's dental impressions are an exact replica of the patients teeth. Most of the dental model materials and techniques cause the model to have variations that will cause the dental restoration to not fit properly in the patient's mouth. There are several techniques and material to make models but all of them have faults that make them time consuming to make or cause inaccurate models.

SUMMARY

From the foregoing discussion, it should be apparent that a need exists for an apparatus and system for dental modeling. Beneficially, such an apparatus and system would make accurate models in less than half the time of traditional dental models. It uses a plastic base brass pin system that eliminates dental stone base expansion which could lead to dental restorations not fitting properly. It also uses a closed bite articulating method which mimics the patients accurate bite which will insure the dental restoration will be in the proper occlusion. As further discussed below, working with the dental model will also be improved by an easy de-articulation feature. In certain embodiments, the pin receptacles on the apparatus have break away caps or covers that when pouring the dental stone onto the base creates an air pocket that does not allow the stone to flow into the open pin holes. The break away covers can be removed to expose the tip of the pin for easy removal of the pinned section. Also a unique pin that holds in place, does not rock and can be pushed out by pushing on one end.

Unlike other pins on the market, the pins of the present disclosure do not rock and holds in place even when pushed out a little. Snapping the articulator together and apart has been an issue for conventional dental models but the present subject matters unique design allows for easy snapping together and disassembling of the articulator hinge. The working pinned side has a tooth outline to insure proper pin and tooth placement.

The present subject matter has been developed in response to the present state of the art, and in particular, in response to the problems and needs in the art that have not yet been fully solved by currently available dental modeling systems. Accordingly, the present subject matter has been developed to provide an apparatus and system for dental modeling that overcomes many or all of the above-discussed shortcomings in the art.

The apparatus for dental modeling, in one embodiment, includes a first tray positioned opposite a second tray and a dearticulating hinge coupling the first tray to the second tray. The dearticulating hinge includes a first hinging element coupled to one of the first tray and the second tray and a second hinging element coupled to the other of the first tray and the second tray. At least one of the first hinging element and the second hinging element includes a disengaging element configured to engage a spur to uncouple the first hinging element from the second hinging element upon extending the first tray and the second tray beyond a predefined angle relative to one another.

In certain embodiments, the first hinging element includes a substantially cylindrical U-channel disposed about a hinging axis. In such an embodiment, the second hinging element includes a C-shaped armature. The C-shaped armature is positionable within the U-channel with the C-shaped armature pivotable around the hinging axis.

In one embodiment, the disengaging element is an end of the C-shaped armature and the spur is an extension extending from a surface within the U-channel. In such an embodiment, the end of the C-shaped armature engages the extension extending from the surface within the U-channel to disengage the C-shaped armature from the U-channel and uncouple the first hinging element from the second hinging element.

In an exemplary embodiment, the first hinging element is a substantially cylindrical member and the second hinging element is at least one C-shaped armature. The at least one C-shaped armature positionable about the cylindrical member and the at least one C-shaped armature is pivotable around the cylindrical member.

The disengaging element, in certain embodiments, is an end of the at least one C-shaped armature and the spur is an extension extending from a surface of the cylindrical member. In such embodiments, the end of the at least one C-shaped armature engages the extension extending from the surface of the cylindrical member to disengage the at least one C-shaped armature from the cylindrical member and uncouple the first hinging element from the second hinging element.

The apparatus also includes, in one embodiment, at least one pin receptacle sized to receive a tray engaging end of at least one pin. In such an embodiment, the at least one pin has a dental appliance engaging end disposed opposite the tray engaging end. In certain embodiments, the at least one pin receptacle includes a plurality of pin receptacles positioned in an arrangement that simulates an arrangement of teeth in at least a portion of a human mouth.

In another embodiment, the apparatus includes a plurality of positioning guides. In certain embodiments, each positioning guide is positioned about a pin receptacle. In such an embodiment each positioning guide indicates an appropriate position of a model of a tooth in an average human mouth.

The apparatus, in another embodiment, includes at least one pin receptacle. The at least one pin receptacle includes a cylindrical portion that maintains a corresponding cylindrical portion of at least one pin in a position substantially parallel to a longitudinal axis through the pin receptacle. In one embodiment, the cylindrical portion of the at least one pin receptacle maintains the corresponding cylindrical portion of the at least one pin in the substantially parallel position to the longitudinal axis through the pin receptacle for a predefined distance as the at least one pin is withdrawn from the at least one pin receptacle.

In a further embodiment, the at least one pin also includes a tapered portion. In such an embodiment, the tapered portion of the at least one pin increases a pressure exerted on the at least one pin receptacle as the at least one pin is positioned deeper within the at least one pin receptacle.

In yet another embodiment, the apparatus includes at least one pin receptacle with the at least one pin receptacle having a pin receiving end and a covered end. In such an embodiment, the covered end includes a removable cover. In one embodiment, the removable cover is removably coupled to the covered end of the at least one receptacle by a frangible material. In an exemplary embodiment, the removable cover forms a liquid tight seal on the covered end of the at least one pin receptacle with the removable cover positioned in a coupled position. The removable cover, in one embodiment, is removed from the at least one pin receptacle by breaking the frangible material coupling the removable cover to the at least one pin receptacle.

An apparatus for dental modeling is also disclosed that includes a first tray, a second tray disposed opposite the first tray, and a plurality of positioning guides in one of the first tray and the second tray. Each positioning guide is positioned about a pin receptacle and each positioning guide indicating an appropriate position of a model of a tooth in an average human mouth.

In another embodiment, the apparatus includes a first tray, a second tray disposed opposite the first tray and at least one pin receptacle in one of the first tray and the second tray. The at least one pin receptacle includes a cylindrical portion with the cylindrical portion of the at least one pin receptacle maintaining a corresponding cylindrical portion of at least one pin in a position substantially parallel to a longitudinal axis through the pin receptacle.

Reference throughout this specification to features, advantages, or similar language does not imply that all of the features and advantages that may be realized with the present subject matter should be or are in any single embodiment of the subject matter. Rather, language referring to the features and advantages is understood to mean that a specific feature, advantage, or characteristic described in connection with an embodiment is included in at least one embodiment of the present subject matter. Thus, discussion of the features and advantages, and similar language, throughout this specification may, but do not necessarily, refer to the same embodiment.

Furthermore, the described features, advantages, and characteristics of the subject matter may be combined in any suitable manner in one or more embodiments. One skilled in the relevant art will recognize that the subject matter may be practiced without one or more of the specific features or advantages of a particular embodiment. In other instances, additional features and advantages may be recognized in certain embodiments that may not be present in all embodiments of the subject matter.

These features and advantages of the present subject matter will become more fully apparent from the following description and appended claims, or may be learned by the practice of the subject matter as set forth hereinafter.

BRIEF DESCRIPTION OF THE DRAWINGS

In order that the advantages of the subject matter will be readily understood, a more particular description of the subject matter briefly described above will be rendered by reference to specific embodiments that are illustrated in the appended drawings. Understanding that these drawings depict only typical embodiments of the subject matter and are not therefore to be considered to be limiting of its scope, the subject matter will be described and explained with additional specificity and detail through the use of the accompanying drawings, in which.

DETAILED DESCRIPTION

Reference throughout this specification to "one embodiment," "an embodiment," or similar language means that a particular feature, structure, or characteristic described in connection with the embodiment is included in at least one embodiment of the present subject matter. Thus, appearances of the phrases "in one embodiment," "in an embodiment," and similar language throughout this specification may, but do not necessarily, all refer to the same embodiment.

Furthermore, the described features, structures, or characteristics of the subject matter may be combined in any suitable manner in one or more embodiments. In the following description, numerous specific details are provided for a thorough understanding of embodiments of the subject matter. One skilled in the relevant art will recognize, however, that the subject matter may be practiced without one or more of the specific details, or with other methods, components, materials, and so forth. In other instances, well-known structures, materials, or operations are not shown or described in detail to avoid obscuring aspects of the subject matter.

Figure 1:
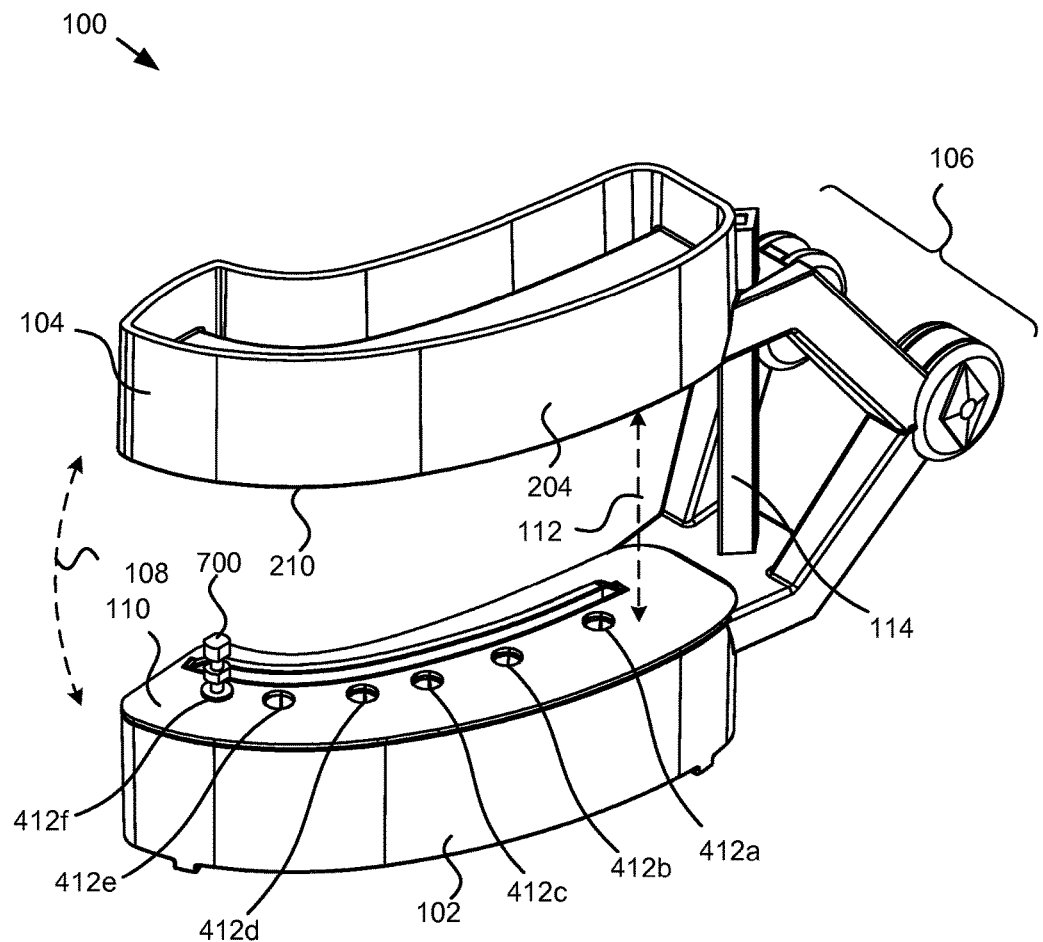
FIG. 1 depicts a perspective view illustrating one embodiment of an apparatus for dental modeling in accordance with the present subject matter.

FIG. 1 depicts a perspective view illustrating one embodiment of an apparatus 100 for dental modeling in accordance with the present subject matter. The apparatus 100, in one embodiment, includes a first tray 102, a second tray 104, and a hinge 106. In certain embodiments, the hinge 106 is a dearticulating hinge that couples the first tray 102 to the second tray 104 allowing the first tray 102 to pivot towards and away from the second tray 104 in the direction indicated by arrow 108.

In certain embodiments, the first tray 102 and the second tray 104 are repositionable with respect to one another in approximately one hundred and eighty degrees (180°) between a closed position and an opened position. In FIG. 1, the apparatus 100 is depicted in a closed position. In the closed position, a dental fixture receiving surface 110 on the first tray 102 faces a dental model receiving channel 202 (FIG. 2) in the second tray 104.

In one embodiment, the dental model receiving channel 202 is defined by a surrounding wall 204 that extends about the periphery of the second tray 104. The surrounding wall 204 extends between a top edge 210 and a bottom edge 212. In such an embodiment, the surrounding wall 204 includes an outer surface 206 and an inner surface 208 with the inner surface 208 defining the dental model receiving channel 202.

In other embodiments, the channel 202 is narrower than the inner surface 208 of the surrounding wall 204 of the second tray 104. For example, with reference to FIG. 3, in one embodiment, the channel 202 is defined by a pair of ledges 302a and 302b disposed along the inner surface 208 of the surrounding wall 204 at each side of surrounding wall 204 such that the channel 202 is positioned along approximately a longitudinal center 304 of the second tray 104. One of skill in the art will recognize that the dashed line 304 representing the approximate longitudinal center 304 is for descriptive purposes only and should not be interpreted to mean any physical structure of the second tray 104.

Referring again to FIG. 1, in the closed position, the top edge 210 of the surrounding wall 204 of the second tray 104 is positioned opposite and substantially parallel with the dental fixture receiving surface 110. In certain embodiments, the dental fixture receiving surface 110 is integral with the first tray 102. In other embodiments, as discussed below, the dental model fixture receiving surface 110 is a surface on a separate dental model receiving insert 600 (see FIG. 6) coupleable to the first tray 102. Throughout this disclosure, the dental receiving surface 110 will be associated with the first tray 102 regardless of whether or not a specific embodiment includes an integral dental fixture receiving surface 110 or a separate dental model receiving insert 600.

Figure 4:
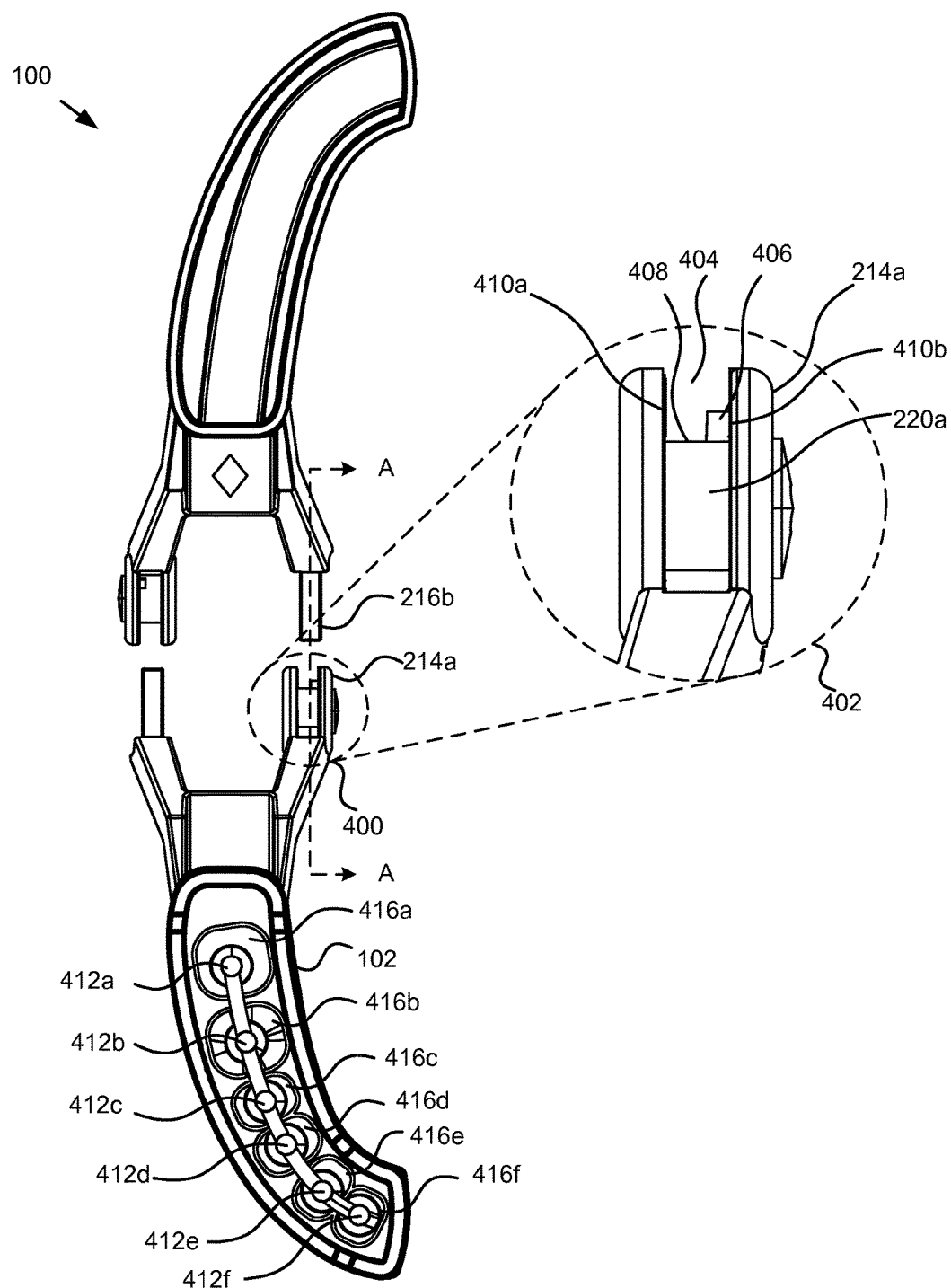
FIG. 4 is a bottom view further illustrating the apparatus of FIGS. 1-3 in accordance with the present subject matter.

The dental model fixture receiving surface 110 of the first tray 102 includes a plurality of pin receptacles 412a-412f (collectively receptacles 412) (see FIG. 4). A pin 700 is depicted as being positioned within pin receptacle 412, the pin 700 and the pin receptacles 412 are further discussed below. In certain embodiments, the pin receptacles 412 are arranged in the shape of at least a portion of an average dental patient's mouth. In other embodiments, the apparatus 100 is shaped to replicate an entire mouth of an average dental patient.

In the closed position, the top edge 210 of the surrounding wall 204 of the second tray 104 is positioned a sufficient distance from the dental fixture receiving surface 110 of the first tray 102 to allow for the dental fixtures to be positioned within a gap 112 between the first tray 102 and the second tray 104. In one embodiment, the gap 112 is at least big enough to accommodate a replica of a dental patient's upper teeth and lower teeth. In other embodiments, the gap 112 is big enough to also accommodate a replica of at least a portion of the dental patient's gums in addition to the replicas of the patient's upper and lower teeth.

In certain embodiments, the apparatus 100 may include a bracing member 114. In such embodiments, in the closed position, the bracing member 114 adds support to the first tray 102 and the second tray 104 to maintain the top edge 210 of the surrounding wall 204 of the second tray 104 in a substantially parallel position relative to the dental fixture receiving surface 110 of the first tray 102.

Figure 2:
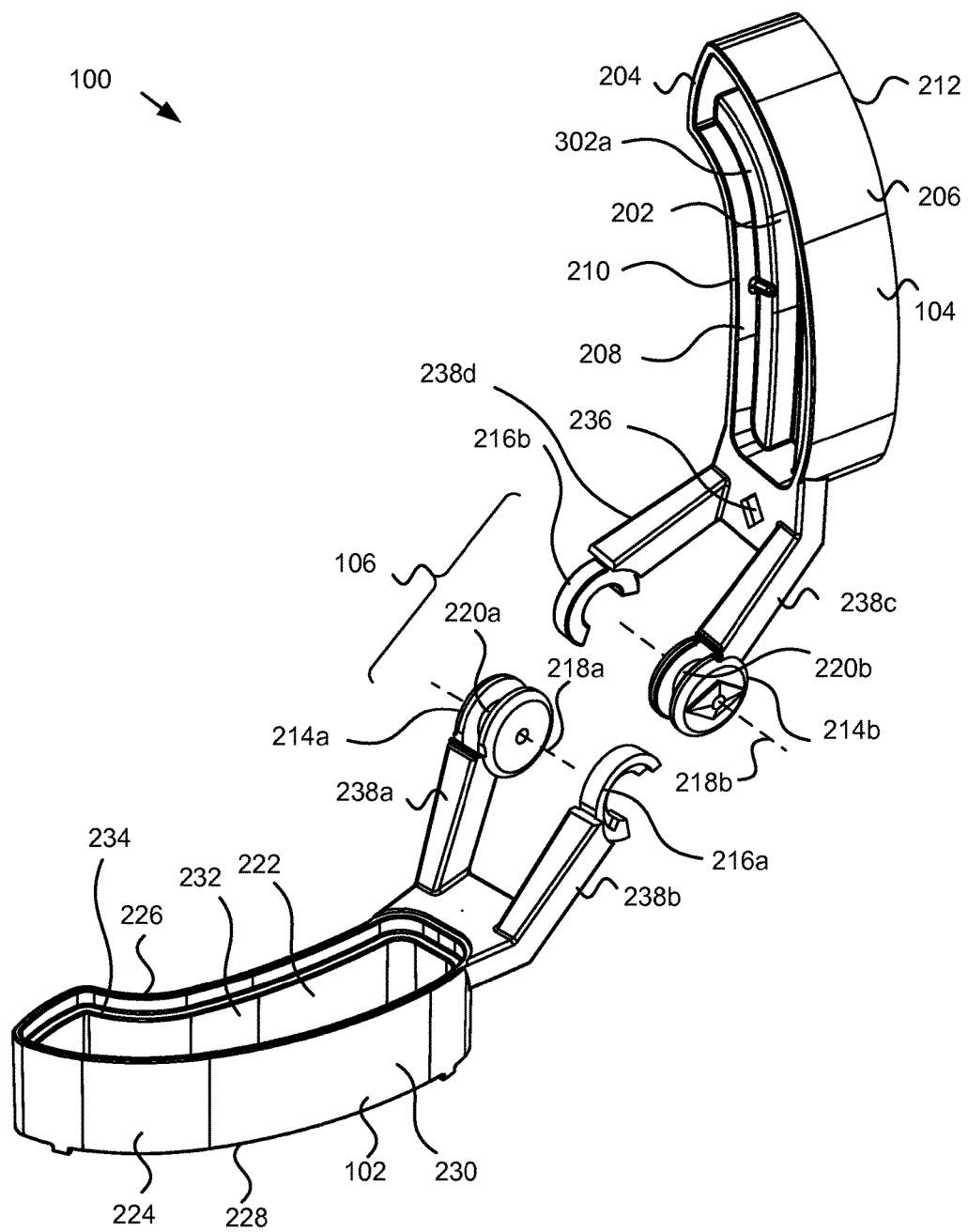
FIG. 2 is a perspective view further illustrating the apparatus of FIG. 1 in accordance with the present subject matter.

FIG. 2 is a perspective view further illustrating the apparatus 100 of FIG. 1 in accordance with the present subject matter. In the embodiment illustrated in FIG. 2, the first tray 102 and the second tray 104 are depicted in an open position with the hinge 106 separated. In other embodiments, in the open position, the first tray 102 remains coupled with the second tray 104. In an exemplary embodiment, as further discussed below, the hinge 106 is disengaged allowing the first tray 102 to be separated from the second tray 104 allowing a clinician to easily manipulate the first tray 102 or the second tray when creating a dental model.

In certain embodiments, the hinge 106 is a dearticulating hinge coupling the first tray 102 to the second tray 102. The dearticulating hinge 106 includes a first hinging element (214a and/or 214b) and a second hinging element (216a and/or 216b). While the embodiment illustrated in FIG. 2 depicts the apparatus 100 as including four hinging elements, first hinging elements 214a and 214b and second hinging elements 216a and 216b, one of skill in the art will recognize that in other embodiments the apparatus may include only two hinging elements hingedly coupling the first tray 102 to the second tray 104.

The first hinging element 214a and/or 214b is coupled to either the first tray 102 or the second tray 104. In other embodiments, such as the embodiment depicted in FIG. 2, the first tray 102 includes a first hinging element 214a and the second tray 104 also includes a first hinging element 214b. In the present disclosure, both hinging elements 214a and 214b are termed a "first hinging element" due to the fact that the physical structure is substantially the same for both hinging elements 214a and 214b. That is, in the embodiment illustrated in FIG. 1, both the first hinging elements 214a and 214b are a U-channel 404 (see FIG. 4) disposed about a cylindrical center portion 220a and 220b having a hinging axis represented by dashed lines 218. In one embodiment, the center portions 220a and 220b of the U-channels 404 of the first hinging elements 214a and 214b are substantially cylindrical and sized to receive the second hinging elements 216b and 216a respectively.

In one embodiment, the second hinging elements 216a and 216b receivable within the U-channels 404 of the first hinging elements 214b and 214a. As with the first hinging elements 214a and 214b, both second hinging elements 216a and 216b are termed a "second hinging element" due to the fact that the physical structure is substantially the same for both second hinging elements 216a and 216b. In the embodiment illustrated in FIG. 1, the second hinging elements 216a and 216b each include a C-shaped armature 502 (see FIG. 5). The C-shaped armatures 502 of the second hinging elements 216a and 216b are receivable within the U-channels of the first hinging elements 214b and 214a respectively. In this position, the C-shaped armatures 502 of the second hinging elements 216a and 216b are pivotable around the hinging axis 218b and 218a of the first hinging elements 214b and 214a respectively.

In one embodiment, each of the first hinging elements 214a and 214b and each of the second hinging elements 216a and 216b are coupled to the first tray 102 and the second tray 104 by one or more arms 238a-238d that extend from the first tray 102 and the second tray 104. While the embodiment illustrated in FIG. 2 depicts the first tray 102 as including a first hinging element 214a and a second hinging element 216a and the second tray 104 as including a first hinging element 214b and a second hinging element 216b, one of skill in the art will recognize that in other embodiments, the first tray 104 may include only one type of hinging element for both hinging elements at the ends of arms 238a and 238b. For example, in one embodiment, both hinging elements on the first tray may be substantially similar to the first hinging elements 214a and 214b. In such an embodiment, the hinging elements at the end of arms 238c and 238d would be substantially similar to the second hinging elements 216a and 216b.

In the embodiment illustrated in FIG. 2, the dental model receiving insert 600 has been removed from the first tray 102 to illustrate an insert receiving space 222 configured to receive the dental model receiving insert 600. In one embodiment, the insert receiving space 222 is defined by a surrounding wall 224 that extends between a top edge 226 and a bottom edge 228. The surrounding wall 224 has an outer surface 230 and an inner surface 232 with the inner surface 232 defining the insert receiving space 222. A ledge 234 extends about the inner surface 232 of the surrounding wall 224. In certain embodiments, the ledge 234 supports the dental model receiving insert 600. In other embodiments, the dental model receiving insert 600 may be supported by the top edge 226 of the surrounding wall 224 of the first tray 102. In such an embodiment, the ledge 234 may be unnecessary and therefore omitted.

As discussed above, in certain embodiments, the first tray 102 may include a dental fixture receiving surface 110 that is integrally molded with the first tray 102. In such an embodiment, the dental model receiving insert 600 may be replaced with the dental fixture receiving surface 110 integrally molded with the first tray 102.

Also illustrated in FIG. 2 is a bracing member receiving aperture 236. In certain embodiments, the bracing member receiving aperture 236 is sized and shaped to receive bracing member 114. Thus, in the embodiment illustrated in FIG. 2, the bracing member receiving aperture 236 has a diamond shape to receive corresponding bracing member 114. In other embodiments, the bracing member 114 and the bracing member receiving aperture 236 may have any other geometric shape. In certain embodiments, the bracing member receiving aperture 236 is sized to be slightly smaller than a profile of the bracing member 114 so that the bracing member receiving aperture 236 tightly holds the bracing member 114 to add support to the apparatus 100 to maintain the top edge 210 of the surrounding wall 204 of the second tray 104 in a substantially parallel position relative to the dental fixture receiving surface 110 of the first tray 102.

Figure 3:
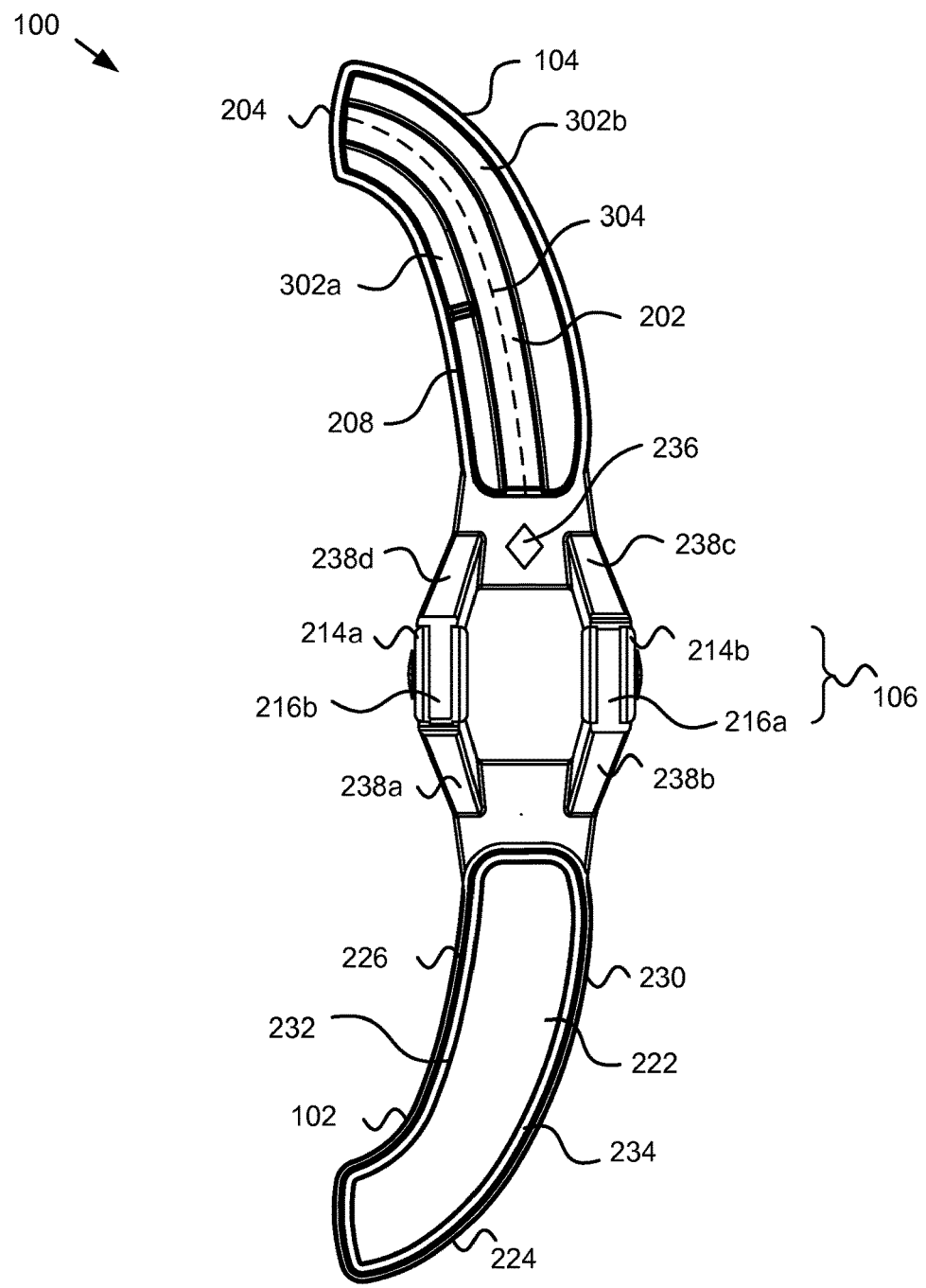
FIG. 3 is a top view further illustrating the apparatus of FIGS. 1 and 2 in accordance with the present subject matter.

FIG. 3 is a top view further illustrating the apparatus 100 of FIGS. 1 and 2 in accordance with the present subject matter. In the embodiment illustrated in FIG. 3, the apparatus 100 is depicted in the open position with the C-shaped armatures 502 of the second hinging elements 216a and 216b positioned within the U-channels 404 of the first hinging elements 214b and 214a respectively. In this position, the first tray 102 and the second tray 104 can pivot about the dearticulating hinge 106 to the open or closed positions discussed above.

Figure 5:
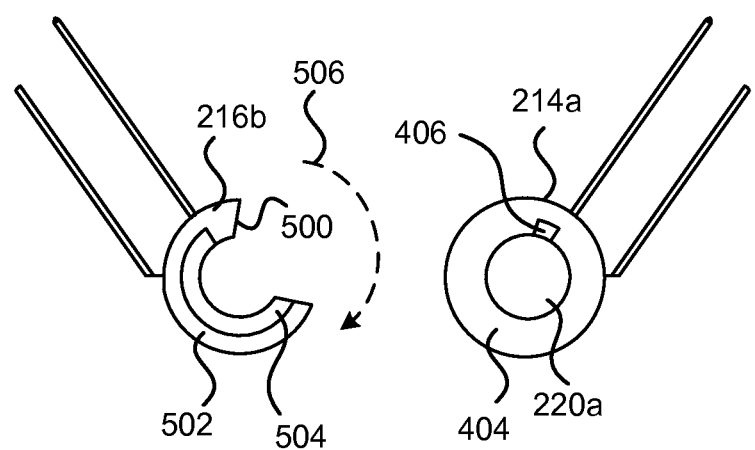
FIG. 5 is a side cutaway view taken along line A-A of FIG. 4 illustrating one embodiment of a dearticulating hinge in accordance with the present subject matter.

FIG. 4 is a bottom view further illustrating the apparatus 100 of FIGS. 1-3 in accordance with the present subject matter. FIG. 5 is a side cutaway view taken along line A-A of FIG. 4 illustrating one embodiment of a dearticulating hinge 106 in accordance with the present subject matter.

In the embodiment illustrated in FIG. 4, area 400 has been enlarged in pop-out 402 to more clearly illustrate features of the first hinging element 214a (and/or 214b). For ease of reference, first hinging element 214a and 214b are collectively referred to herein as first hinging element or elements 214 and second hinging elements 216a and 216b are collectively referred to herein as second hinging element or elements 216.

In certain embodiments, the first hinging element 214 includes a U-channel 404 disposed about a substantially cylindrical center portion 220a. In one embodiment, a spur 406 is disposed within the U-shaped channel and operates in cooperation with a disengaging element 500 to uncouple the first hinging element 214 from the second hinging element 216.

As more clearly depicted in FIG. 5, in certain embodiments, the second hinging element 216b includes a C-shaped armature 502 that is positionable around the cylindrical center portion 220a of the first hinging element 214a. The cylindrical center portion 220a of the first hinging element 214a pivots within the C-shaped armature 502 of the second hinging element 216b to impart a hinging action to the first hinging element and the second hinging element 216b.

In one embodiment, the C-shaped armature 502 includes a groove 504 that extends around at least a portion of the inner diameter of the C-shaped armature 502. The groove 504 allows the C-shaped armature 502 of the second hinging element 216b to pivot around the cylindrical center portion 220a of the first hinging element 214a without interference from the spur 406 in the first hinging element 214a.

As the C-shaped armature 502 of the second hinging element 216b is pivoted around the cylindrical center portion 220a of the first hinging element 214a in the direction indicated by arrow 506, the disengaging element 500 of the second hinging element 216b is forced into contact with the spur 406 in the first hinging element 214a. Further rotating of the second hinging element 216b in the direction of arrow 506 causes the spur 406 and the disengaging element 500 to pry the cylindrical center portion 220a of the first hinging element 214a out of the C-shaped armature 502 of the second hinging element 216b.

In certain embodiments, the disengaging element 500 is an end of the C-shaped armature 502 and the spur 406 is an extension extending from a surface within the U-channel 404. In such an embodiment, the end of the C-shaped armature 502 engages the extension (the spur 406) extending from the surface within the U-channel 404 to disengage the C-shaped armature 502 from the U-channel 404 and uncouple the first hinging element 102 from the second hinging element 104.

One of skill in the art will recognize that the spur 406 and the disengaging element 500 can be positioned either on the first hinging element 214a or the second hinging element 216b. Therefore, in certain embodiments, at least one of the first hinging element 214a and/or 214b and the second hinging element 216a and/or 216b includes a disengaging element 500 configured to engage a spur 406 to uncouple the first hinging element 214a and/or 214b from the second hinging element 216a and/or 216b. In one embodiment, the disengaging action between occurs upon extending the first tray 102 and the second tray 104 beyond a predefined angle relative to one another. In certain embodiments, the predefined angle is an angle that causes the disengaging element 500 to come into contact with the spur. In one embodiment, the predefined angle is an angle that positions the a dental fixture receiving surface 110 of the first tray 102 one hundred and eighty degrees (180°) from the top edge 210 of the second tray 104.

The embodiments illustrated in FIG. 4 depicts the U-channel as having a floor 408 surrounded by walls 410a and 410b with the walls 410a and 410b extending perpendicularly from the floor 408. In other embodiments, the walls 410a and 410b may extend from the floor 408 at an angle other than perpendicular. In yet another embodiment, the walls 410a and 410b may curve as they approach the floor 408.

FIG. 4 also depicts the first tray 102 as including a plurality of pin receptacles 412a-412f (collectively receptacles 412). In certain embodiments, the pin receptacles 412 are arranged in the shape of at least a portion of an average dental patient's mouth. In other embodiments, the apparatus 100 is shaped to replicate an entire mouth of an average dental patient. Accordingly, in certain embodiments, the pin receptacles 412 are positioned in an arrangement that simulates an arrangement of teeth in at least a portion of a human mouth.

In certain embodiments, the dental model receiving insert 600 (or a surface 414 opposite the dental fixture receiving surface 110 on the first tray 102) is transparent. In such embodiments, a clinician can look through the dental model receiving insert 600 or surface 414 to align a mold of at least a portion of a dental patient's mouth with at least one of the pin receptacles 412.

In one embodiment, the dental model receiving insert 600 or surface 414 includes a plurality of positioning guides 416a-416f (collectively positioning guides 416). Each positioning guide 416 is disposed about one of the pin receptacles 412 and indicates an appropriate position for a model of a tooth in an average human mouth. In certain embodiments, the positioning guides 416a-416f are shaped substantially similar to a profile of a tooth located at that position in an average users human mouth. Thus, in certain embodiments, the positioning guides 416 and/or the pin receptacles 412 help a clinician orient a model of at least a portion of a dental patient's mouth with the first tray 102.

Figure 6:
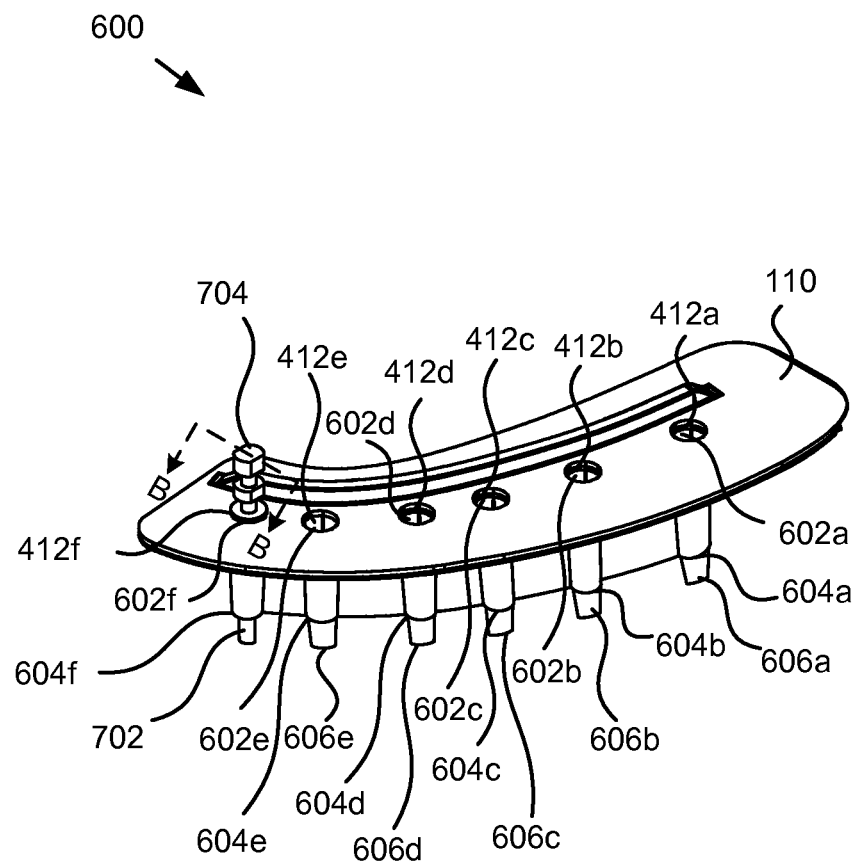
FIG. 6 depicts a perspective view illustrating one embodiment of a dental model receiving insert in accordance with the present subject matter.

FIG. 6 depicts a perspective view illustrating one embodiment of a dental model receiving insert 600 in accordance with the present subject matter. In certain embodiments, the dental model receiving insert 600 includes a plurality of pin receptacles 412a-412f. Each pin receptacle 412 is sized to receive a tray engaging portion 706 (see FIG. 7) of a tray engaging end 702 (see FIG. 7) of a pin 700 (see FIG. 7).

The pin receptacles 412 have a pin receiving end 602a-602f (collectively pin receiving ends 602) and a covered end 604a-604e (collectively covered ends 604). The covered ends 604 include a removable cover 606a-606e (in the embodiment illustrated in FIG. 6, a pin 700 is positioned within pin receptacle 412f and the cover 606 has been removed from pin receptacle 412f). In certain embodiments, the removable covers 606a-606e are coupled to the covered ends 604a-604e of the pin receptacle 412a-412f by a frangible material that forms a liquid tight seal on the covered ends 604a-604e of the pin receptacles 412a-412f with the removable covers 606a-606e positioned in a coupled position. In such an embodiment, the removable covers 606a-606f are removed from the pin receptacles 412a-412f by breaking the frangible material coupling the removable covers 606a-606f to the at least one pin receptacle 412a-412f.

In this manner, when a clinician pores a molding substance (i.e., plaster) into a mold positioned on the dental model receiving insert 600 the molding substance does not travel through any of the covered ends 604a-604e of the pin receptacles 412a-412f. This keeps the molding substance from areas within the apparatus 100 that should remain free from the molding substance.

Figure 7:
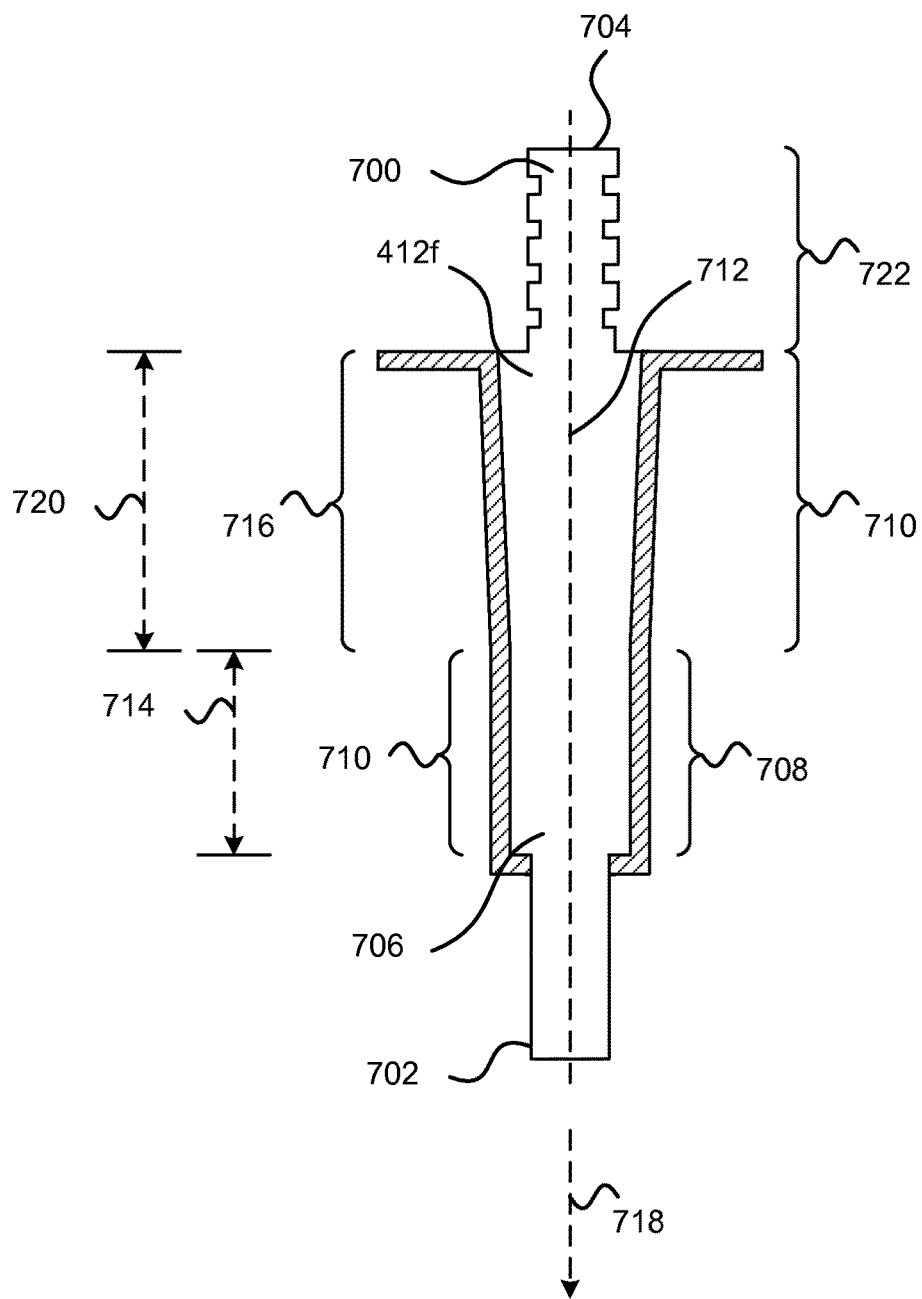
FIG. 7 is a side cutaway view taken along line B-B of FIG. 6 illustrating one embodiment of a pin positioned within a pin receptacle in accordance with the present subject matter.

FIG. 7 is a side cutaway view taken along line B-B of FIG. 6 illustrating one embodiment of a pin 700 positioned within a pin receptacle 412f in accordance with the present subject matter. In certain embodiments, the pin receptacle 412f is sized to receive a tray engaging portion 706 of a tray engaging end 702 of the pin 700. The pin 700 has a dental appliance engaging end 704 disposed opposite the tray engaging end 702.

In one embodiment, the pin receptacle 412f includes a cylindrical portion 708 that maintains a corresponding cylindrical portion 710 of the pin 700 in a position substantially parallel to a longitudinal axis 712 through the pin receptacle 412f. In an exemplary embodiment, the cylindrical portion 708 of the pin receptacle 412f maintains the corresponding cylindrical portion 710 of the pin 700 in the parallel position for a predefined distance (i.e., for the length 714 of the cylindrical portion 710 of the pin 700) as the pin 700 is withdrawn from the pin receptacle 412f. In one embodiment, length 714 of the cylindrical portion 710 is approximately four millimeters (4 mm). In certain embodiments, the diameter of the cylindrical portion 710 of the pin 700 is about 2.39 mm.

In certain embodiments, the pin 700 also includes a tapered portion 716. In such embodiments, the tapered portion 716 of the pin 700 increases a pressure exerted on the pin receptacle 412f as the pin 700 is positioned deeper within the pin receptacle 412f. Thus, as the pin 700 is pushed deeper within the pin receptacle 412f in the direction of arrow 718, the pin 700 is lodged tighter within the pin receptacle 412f. In an exemplary embodiment, the length 720 of the tapered portion 716 of the pin 700 is approximately six millimeters (6 mm). In certain embodiments, the diameter of a top of the tapered portion 716 of the pin 700 is about 3 mm.

In one embodiment, a dental fixture engagement portion 722 of the pin 700 has a length of about four (4 mm) and a varying diameter, with the largest diameter of the dental fixture engagement portion 722 of the pin 700 being about 1.25 mm and the smallest diameter of the dental fixture engagement portion 722 of the pin 700 being about 1.75 mm. An extending portion 724 of the pin 700 has a length of about four (4 mm) and a diameter varying from about 1.65 mm to about 1.5 mm with the larger diameter being the diameter of the extending portion 714 of the pin 700 at a position adjacent the cylindrical portion 710 of the pin 700.

The present subject matter may be embodied in other specific forms without departing from its spirit or essential characteristics. The described embodiments are to be considered in all respects only as illustrative and not restrictive. The scope of the subject matter is, therefore, indicated by the appended claims rather than by the foregoing description. All changes which come within the meaning and range of equivalency of the claims are to be embraced within their scope.

What is claimed is:

1. An apparatus for dental modeling, the apparatus comprising:
   a first tray;
   a second tray disposed opposite the first tray; and
   a dearticulating hinge coupling the first tray to the second tray, the dearticulating hinge comprising a first hinging element coupled to one of the first tray and the second tray and a second hinging element coupled to the other of the first tray and the second tray, at least one of the first hinging element and the second hinging element comprising a disengaging element configured to engage a spur to uncouple the first hinging element from the second hinging element upon extending the first tray and the second tray beyond a predefined angle relative to one another, wherein the first hinging element comprises a substantially cylindrical U-channel disposed about a hinging axis and wherein the second hinging element comprises a C-shaped armature, the C-shaped armature disposed within the U-channel, wherein the C-shaped armature is pivotable around the hinging axis, wherein the disengaging element comprises an end of the C-shaped armature and wherein the spur comprises an extension extending from a surface within the U-channel, wherein the end of the C-shaped armature engages the extension extending from the surface within the U-channel to disengage the C-shaped armature from the U-channel and uncouple the first hinging element from the second hinging element.

2. The apparatus of claim 1, wherein the first hinging element comprises a substantially cylindrical member and wherein the second hinging element comprises at least one C-shaped armature, the at least one C-shaped armature disposed about the cylindrical member, wherein the at least one C-shaped armature is pivotable around the cylindrical member.

3. The apparatus of claim 2, wherein the disengaging element comprises an end of the at least one C-shaped armature and wherein the spur comprises an extension extending from a surface of the cylindrical member, wherein the end of the at least one C-shaped armature engages the extension extending from the surface of the cylindrical member to disengage the at least one C-shaped armature from the cylindrical member and uncouple the first hinging element from the second hinging element.

4. The apparatus of claim 1, further comprising at least one pin receptacle sized to receive a tray engaging end of at least one pin, the at least one pin having a dental appliance engaging end disposed opposite the tray engaging end.

5. The apparatus of claim 4, wherein the at least one pin receptacle comprises a plurality of pin receptacles positioned in an arrangement that simulates an arrangement of teeth in at least a portion of a human mouth.

6. The apparatus of claim 5, further comprising a plurality of positioning guides, each positioning guide disposed about a pin receptacle, each positioning guide indicating an appropriate position of a model of a tooth in an average human mouth.

7. The apparatus of claim 1, further comprising at least one pin receptacle, the at least one pin receptacle comprising a cylindrical portion, the cylindrical portion of the at least one pin receptacle maintaining a corresponding cylindrical portion of at least one pin in a position substantially parallel to a longitudinal axis through the pin receptacle.

8. The apparatus of claim 7, wherein the cylindrical portion of the at least one pin receptacle maintains the corresponding cylindrical portion of the at least one pin in the substantially parallel position to the longitudinal axis through the pin receptacle for a predefined distance as the at least one pin is withdrawn from the at least one pin receptacle.

9. The apparatus of claim 7, wherein the at least one pin comprises a tapered portion, the tapered portion of the at least one pin increasing a pressure exerted on the at least one pin receptacle as the at least one pin is positioned deeper within the at least one pin receptacle.

10. The apparatus of claim 1, further comprising at least one pin receptacle, the at least one pin receptacle comprising a pin receiving end and a covered end, the covered end having a removable cover.

11. The apparatus of claim 10, wherein the removable cover is removably coupled to the covered end of the at least one receptacle by a frangible material, the removable cover forming a liquid tight seal on the covered end of the at least one pin receptacle with the removable cover positioned in a coupled position.

12. The apparatus of claim 10, wherein the removable cover is removed from the at least one pin receptacle by breaking the frangible material coupling the removable cover to the at least one pin receptacle.

* * * * *